(12) United States Patent
Urayama et al.

(10) Patent No.: US 8,097,737 B2
(45) Date of Patent: Jan. 17, 2012

(54) PROCESS FOR PRODUCTION OF OPTICALLY ACTIVE AMINE DERIVATIVES

(75) Inventors: Shinichi Urayama, Osaka (JP); Eigo Mutou, Osaka (JP); Atsushi Inagaki, Osaka (JP); Takashi Okada, Hikari (JP); Shigeharu Sugisaki, Dublin (IE)

(73) Assignee: Takeda Pharmaceutical Company Limited, Fujisawa-Shi (JP)

( * ) Notice: Subject to any disclaimer, the term of this patent is extended or adjusted under 35 U.S.C. 154(b) by 796 days.

(21) Appl. No.: 11/662,684

(22) PCT Filed: Sep. 12, 2005

(86) PCT No.: PCT/JP2005/016761
§ 371 (c)(1),
(2), (4) Date: Sep. 12, 2008

(87) PCT Pub. No.: WO2006/030739
PCT Pub. Date: Mar. 23, 2006

(65) Prior Publication Data
US 2009/0036521 A1 Feb. 5, 2009

(30) Foreign Application Priority Data
Sep. 13, 2004 (JP) .................................. 2004-265307

(51) Int. Cl.
*C07D 307/93* (2006.01)
(52) U.S. Cl. ........................................................ 549/458
(58) Field of Classification Search .................... 549/458
See application file for complete search history.

(56) References Cited

U.S. PATENT DOCUMENTS

| 6,034,239 | A | 3/2000 | Ohkawa et al. |
| 6,348,485 | B1 | 2/2002 | Ohkawa et al. |
| 2004/0018239 | A1 | 1/2004 | Ishida et al. |

FOREIGN PATENT DOCUMENTS

| EP | 0 812 835 A1 | 12/1997 |
| EP | 1 199 304 | 4/2002 |
| JP | 10-287665 | 10/1998 |
| JP | 11-80106 | 3/1999 |
| JP | 11-140073 | 5/1999 |
| JP | 2000-63272 | 2/2000 |
| JP | 2002-212063 | 7/2002 |
| WO | WO-96/26201 | 8/1996 |
| WO | WO-99/63977 | 12/1999 |

OTHER PUBLICATIONS

R. A. Baxter et al., "Furochromones. Part I. The Synthesis of Khellin," *J. Chem. Soc.*, pp. S30-S32 (1949).
D. Hellwinkel et al., "Palladiumacetat-vermittelte Cyclisierung von di- und tri-funktionellen Triarylaminen, Diarylethern und Diarylketonen," *Liebigs Ann. Chem.*, pp. 945-949 (1989).
J. M. Davidson et al., "Reaction of Metal Ion Complexes with Hydrocarbons. Part 1. 'Palladation' and Some Other New Electrophilic Substitution Reactions. The Preparation of Palladium(1)," *J. Chem. Soc. (A)*, pp. 1324-1330 (1968).
J. D. Ballantine et al., "Synthetic Steriods. Part XI. 1 Stereochemistry of the TiffeneauDemjanov Ring Expansion of 5α-Cholestan-3-one," *J. Chem. Soc. (C)*, pp. 736-738 (1970).
Ramelteon [USAN], RN: 196597-26-9, MW: 259.347, *National Library of Medicine*, http://chem.sis.nlm.nih.gov/chemidplus/jsp/common/ChemFull.jsp?MW=259.347, Jun. 10, 2006.
N. Tarui et al., "Kinetic Resolution of an Indan Derivative Using *Bacillus* sp. SUI-12: Synthesis of a Key Intermediate of the Melatonin Receptor Agonist TAK-375," *Journal of Bioscience and Bioengineering*, vol. 93(1), pp. 44-47 (2002).
K. Chilman-Blair, et al: "Treatment of Insomnia Treatment of Circadian Rhythm Disorders Melatonin MT1/MT2 Agonist", Drugs of the Future 2003, 28(10): 950-958.
Osamu Uchikawa, et al: "Synthesis of a Novel Series of Tricyclic Indan Derivatives as Melatonin Receptor Agonists", J. Med. Chem. 2002, 45, 4222-4239.
European Search Report for corresponding European Application No. 05782085.4 dated Nov. 12, 2009.

*Primary Examiner* — Taofiq A Solola
(74) *Attorney, Agent, or Firm* — Edwards Wildman Palmer LLP; David G. Conlin; Dwight D. Kim

(57) ABSTRACT

An industrial process for production of high-purity optically active amine derivatives in high yield while inhibiting the formation of by-products, which comprises subjecting (E)-2-(1,6,7,8-tetrahydro-2H-indeno[5,4-b]furan-8-ylidene)ethylamine to asymmetric reduction, catalytically reducing the obtained product at a reaction temperature of 40 to 100° C. and a pH of 3 to 9, subjecting the obtained (S)-2-(1,6,7,8-tetrahydro-2H-indeno[5,4-b]furan-8-yl)ethylamine to propionylation, and then crystallizing the reaction mixture.

5 Claims, 1 Drawing Sheet

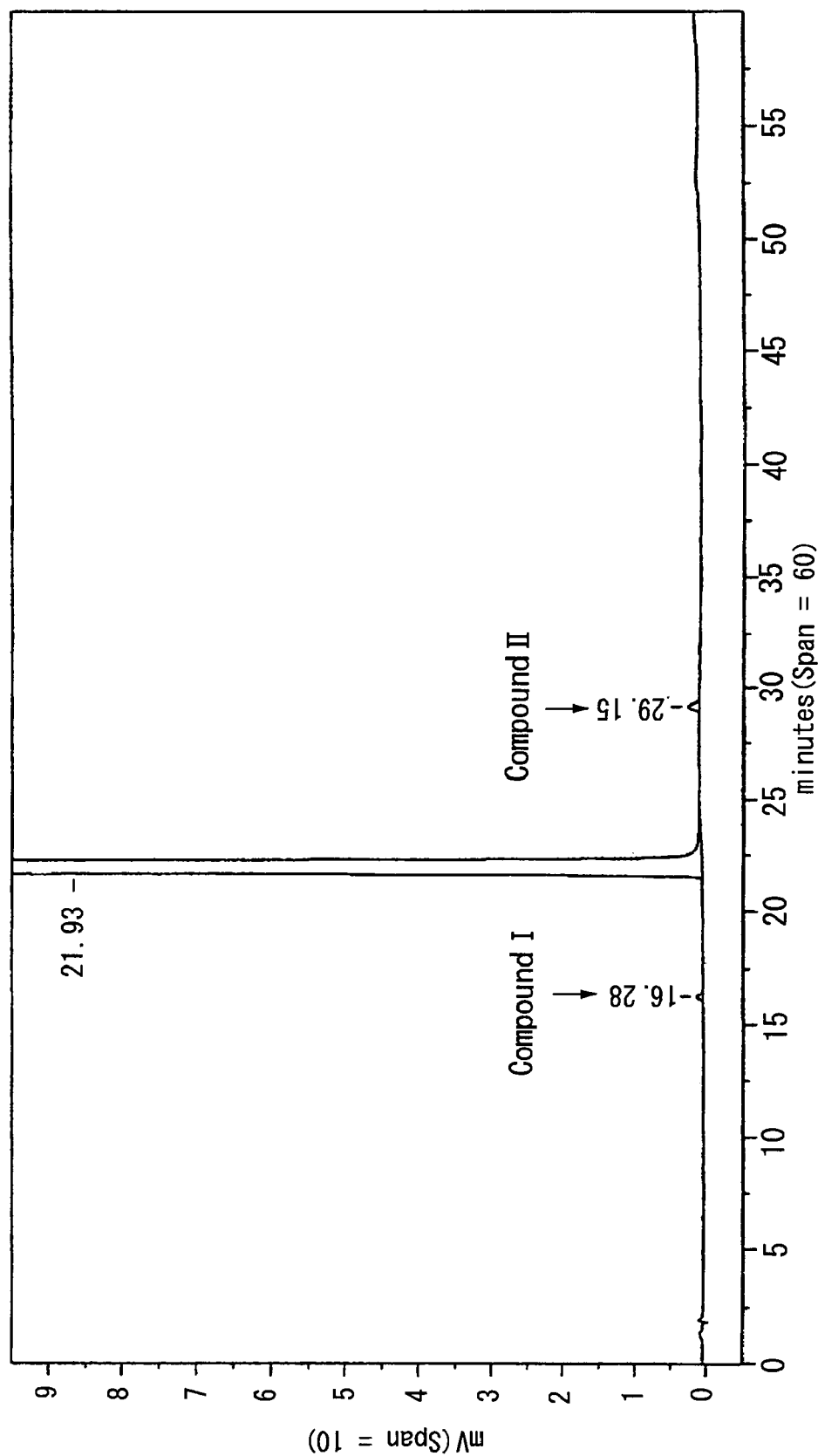

PROCESS FOR PRODUCTION OF OPTICALLY ACTIVE AMINE DERIVATIVES

TECHNICAL FIELD

The present invention relates to a process for production of an optically active amine derivative having high purity, wherein the formation of side products is suppressed.

BACKGROUND ART

Although JP-A 11-140073 and JP-A 2002-212063 disclose a method for producing (S)-2-(1,6,7,8-tetrahydro-2H-indeno[5,4-b]furan-8-yl)ethylamine hydrochloride by means of asymmetric reduction from (E)-2-(1,6,7,8-tetrahydro-2H-indeno[5,4-b]furan-8-ylidene)ethylamine hydrochloride as starting material, both methods are not enough as an industrial production method in which the formation of side products is suppressed and high-purity crystals of (S)-2-(1,6,7,8-tetrahydro-2H-indeno[5,4-b]furan-8-yl)ethylamine hydrochloride are produced with high yield. In particular, problems are to control the side products represented by the following formulae (III') and (IV').

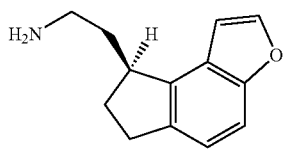
(III')

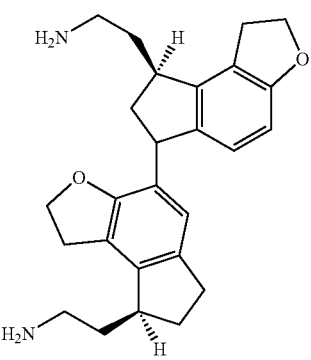
(IV')

On the other hand, dimerization of benzofuran compound under the presence of Pd-catalyst is described in Liebigs. Ann. Chem., 10,945 (1989) and J. Chem. Soc. (A), 1324 (1968). However, these cases are the dimerization by binding of two aromatic rings, and the structures of their dimers are different from those of dimers formed by the reaction between aromatic ring and benzyl position, like compound represented by the above formula (IV'). In addition, J. Chem. Soc. D, 736. (1970) discloses that oxidation of benzyl position of benzofuran compound takes place under the presence of Pd-catalyst, but formation of dimer is not described therein.

DISCLOSURE OF INVENTION

The object of the present invention is to provide an industrial process for production of an optically active amine derivative with high yield and high purity, wherein the formation of side products is controlled.

As a result of intensive studies to solve the above problem, the present inventors found that in the steps of production of the optically active amine derivative, the formation of side products represented by the above formulae (III') and (IV') can be controlled by controlling pH and temperature of the reaction solution at the time of catalytic reduction with Pd—C and the solution at the time of post-treatment thereof, and completed the present invention.

That is, the present invention provides:

(1) A process for producing (S)-2-(1,6,7,8-tetrahydro-2H-indeno[5,4-b]furan-8-yl)ethylamine or a salt thereof, which comprises step (i): a step for asymmetrically reducing (E)-2-(1,6,7,8-tetrahydro-2H-indeno-[5,4-b]furan-8-ylidene)ethylamine or a salt thereof with a catalyst, and step (ii): a step for catalytically reducing the reaction product obtained in step (i) at a reaction temperature of 40° C. to 100° C. and pH 3 to 9 with a catalyst, (2) The process according to the above-mentioned (1), wherein the reaction temperature in step (ii) is 50° C. to 70° C., (3) The process according to the above-mentioned. (1), wherein the pH in step (ii) is 5 to 7, (4) The process according to the above-mentioned (1), wherein the catalyst in step (i) is Ru-BINAP catalyst, (5) The process according to the above-mentioned (1), wherein the catalyst in step (ii) is Pd—C catalyst, (6) A process for producing crystals of (S)—N-[2-(1,6,7,8-tetrahydro-2H-indeno[5,4-b]furan-8-yl)ethyl]propionamide, comprising step (a): a step for propionylating the amino group of (S)-2-(1,6,7,8-tetrahydro-2H-indeno[5,4-b]furan-8-yl)ethylamine or a salt thereof obtained in the process according to the above-mentioned (1), and step (b): a step for crystallizing by adding aqueous solvent to the reaction solution obtained in step (a), (7) Crystals of (S)-N-[2-(1,6,7,8-tetrahydro-2H-indeno[5,4-b]furan-8-yl)ethyl]propionamide, wherein each content of the compounds represented by the following formulae (I), (II), (III) and (IV) is 0.15% by weight or less, and the total content of the compounds represented by the following formulae (I) to (IV) is 0.2% by weight or less,

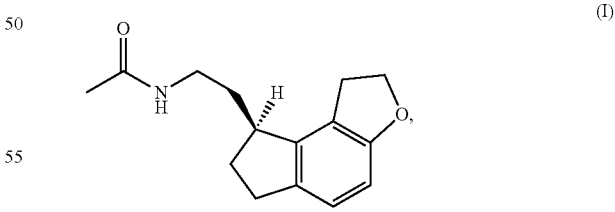
(I)

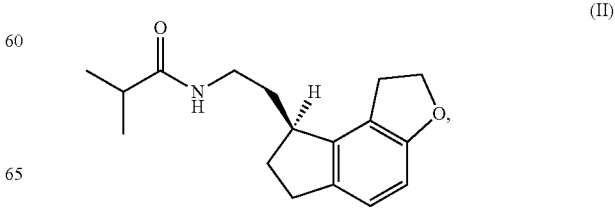
(II)

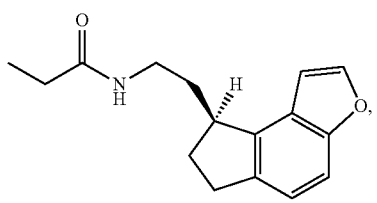
(III)

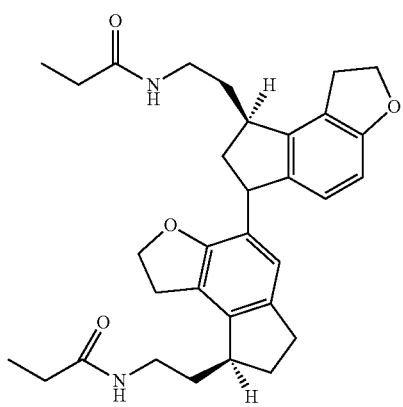
(IV)

(8) Crystals of (S)—N-[2-(1,6,7,8-tetrahydro-2H-indeno[5,4-b]furan-8-yl)ethyl]propionamide, wherein each content of the compounds represented by the following formulae (I), (III) and (IV) is 0.15% by weight or less, and the content of the compound represented by the following formula (II) is 0.02 to 0.15% by weight, and further the total content of the compounds represented by the following formulae (I) to (IV) is 0.2% by weight or less,

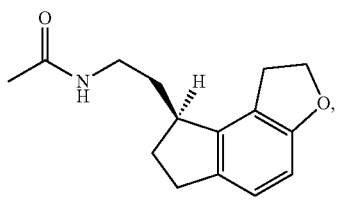
(I)

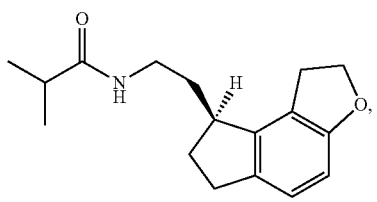
(II)

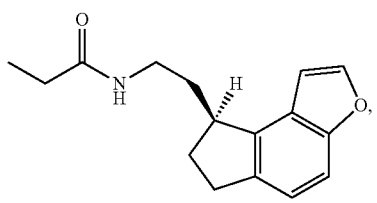
(III)

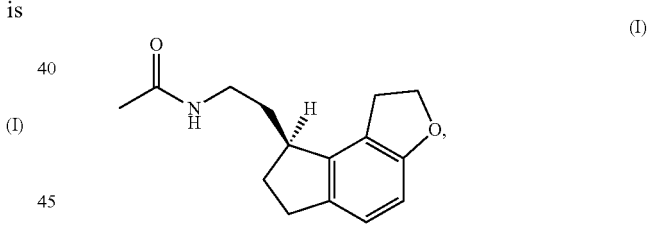
(IV)

(9) The crystals according to the above-mentioned (7) or (8), wherein the content of the compound represented by formula (I) is 0.10% by weight or less,

(10) A composition comprising (S)—N-[2-(1,6,7,8-tetrahydro-2H-indeno[5,4-b]furan-8-yl)ethyl]propionamide and the compounds represented by the following formulae (I), (II), (III) and (IV), wherein relative to 100 parts by weight of (S)—N-[2-(1,6,7,8-tetrahydro-2H-indeno[5,4-b]furan-8-yl)ethyl]propionamide, each content of the compounds represented by the following formulae (I), (II), (III) and (IV) is 0 to 0.15 part by weight and the total content of the compounds represented by the following formulae (I) to (IV) is 0 to 0.2 part by weight,

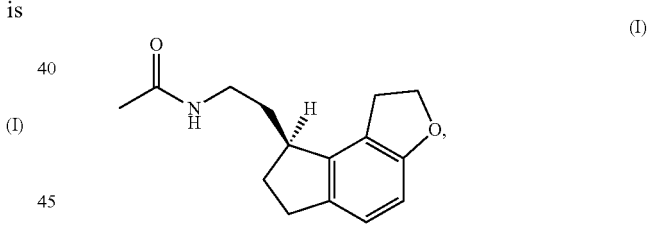
(I)

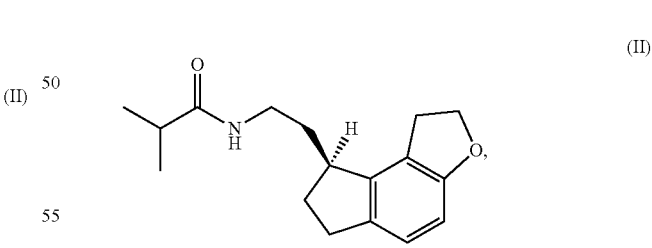
(II)

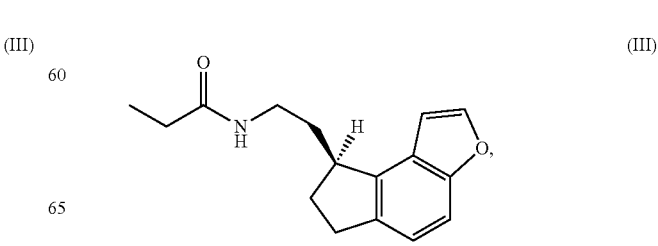
(III)

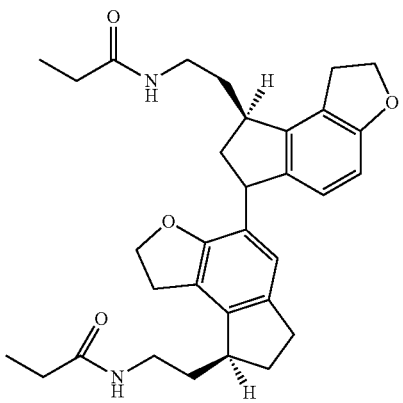

(11) A composition comprising (S)—N-[2-(1,6,7,8-tetrahydro-2H-indeno[5,4-b]furan-8-yl)ethyl]propionamide and the compounds represented by the following formulae (I), (II), (III) and (IV), wherein relative to 100 parts by weight of (S)—N-[2-(1,6,7,8-tetrahydro-2H-indeno[5,4-b]furan-8-yl)ethyl]propionamide, each content of the compounds represented by the following formulae (I), (III) and (IV) is 0 to 0.15 part by weight, and the content of the compound represented by the following formula (II) is 0.02 to 0.15 part by weight, and further the total content of the compounds represented by the following formulae (I) to (IV) is 0 to 0.2 part by weight,

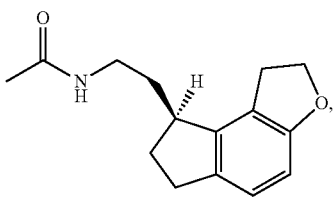

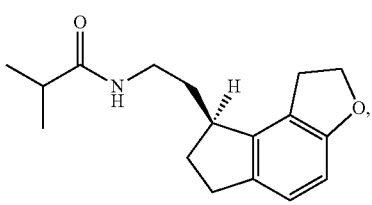

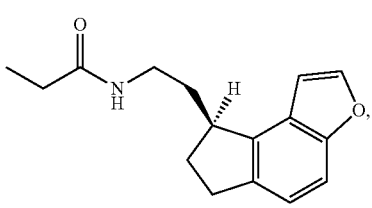

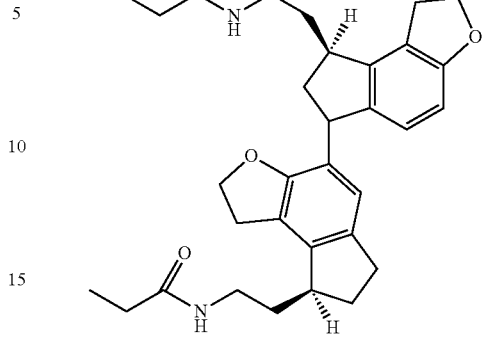

(12) The composition according to the above-mentioned (10) or (11), wherein the content of the compound represented by formula (I) is 0 to 0.10 part by weight relative to 100 parts by weight of (S)—N-[2-(1,6,7,8-tetrahydro-2H-indeno[5,4-b]furan-8-yl)ethyl]propionamide,

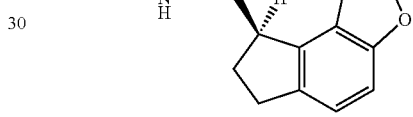

(13) The crystals according to the above-mentioned (7) or the composition according to the above-mentioned (10), which is prepared on a commercial scale,

(14) A process for producing 1,2,6,7-tetrahydro-8H-indeno[5,4-b]furan-8-one, comprising a step for reducing 4,5-dibromo-1,2,6,7-tetrahydro-8H-indeno[5,4-b]furan-8-one with Pd—C catalyst under the condition:

hydrogen pressure (MPa)>−0.02×gas-liquid overall mass transfer volume coefficient (1/hr)+0.43,

(15) Use of the crystals according to the above-mentioned (7) for the manufacture of a preventive or therapeutic agent for sleep disorder,

(16) The composition according to the above-mentioned (10) which is a preventive or therapeutic agent for sleep disorder, and

(17) A method for the prevention or treatment of sleep disorder, comprising administering the crystals according to the above-mentioned (8) or the composition according to the above-mentioned (10).

BRIEF DESCRIPTION OF DRAWINGS

FIG. 1 is a HPLC chart which shows result of analysis of compound (I) to (IV) in the crystals of (S)—N-[2-(1,6,7,8-tetrahydro-2H-indeno[5,4-b]furan-8-yl)ethyl]propionamide.

BEST MODE FOR CARRYING OUT THE INVENTION

Examples of the salt of (S)-2-(1,6,7,8-tetrahydro-2H-indeno[5,4-b]furan-8-yl)ethylamine in the present invention include salts with an inorganic acid such as hydrochloric acid, sulfuric acid, and nitric acid, salts with an organic acid such as formic acid, acetic acid, and trifluoroacetic acid, and the like.

In addition, (E)-2-(1,6,7,8-tetrahydro-2H-indeno[5,4-b]furan-8-ylidene)ethylamine which is a raw compound to be used for the production of (S)-2-(1,6,7,8-tetrahydro-2H-indeno[5,4-b]furan-8-yl)ethylamine or a salt thereof of the present invention can be produced by a method described in JP-A 2002-212063, that is, method of catalytically reducing 4,5-dibromo-1,2,6,7-tetrahydro-8H-indeno[5,4-b]furan-8-one with catalytic reduction catalyst such as Pd—C, then reacting the obtained 1,2,6,7-tetrahydro-8H-indeno[5,4-b]-furan-8-one with diethyl cyanomethylphosphonate, followed by hydrogenating with cobalt catalyst, or analogous methods thereto.

In the catalytic reduction step, catalytic reduction of 4,5-dibromo-1,2,6,7-tetrahydro-8H-indeno[5,4-b]furan-8-one can be carried out by mixing 4,5-dibromo-1,2,6,7-tetrahydro-8H-indeno[5,4-b]furan-8-one, organic solvent, and if desired, a base, then preferably after displacing the system with nitrogen, adding catalytic reduction catalyst thereto, followed by pressurizing with hydrogen and stirring.

Here, from the viewpoint of formation control of side product (specifically, dimer), it is preferred that the reaction should be carried out under the condition of hydrogen pressure and gas-liquid overall mass transfer volume coefficient, which meets the inequality:

$$\text{hydrogen pressure (MPa)} \geq -0.02 \times \text{gas-liquid overall mass transfer volume coefficient (1/hr)} + 0.43.$$

Herein, the gas-liquid overall mass transfer volume coefficient can be determined with $Na_2SO_3$ method as described in detail in the after-mentioned Example 1.

Further, the hydrogen pressure in the present reaction is usually 0.1 to 1 MPa, preferably 0.3 to 0.5 MPa.

In gas-liquid system, rate $N_A$ in which gas dissolves in solution per unit contact area can be expressed like in the case of dissolution rate in solid-liquid system, extraction rate in liquid-liquid system and transfer phenomenon in heat transfer by convection, and given in the form of (mass transfer coefficient)×(concentration difference).

$$N_A = K_L(C_1 - C) \quad (1)$$

Here, $K_L$ is a mass transfer coefficient for liquid, $C_1$ is a concentration which is in equilibrium with gas partial pressure in gas bubble and C is a saturated concentration at a given time, and $(C_1 - C)$ is a driving force for gas absorption.

In addition, given that A is a gas-liquid contact area and $V_L$ is a volume of liquid, since increasing rate $V_L dC/dt$ of gas concentration in solution is equal to dissolution rate of gas, the following equation can be given.

$$N_A A = V_L dC/dt \quad (2)$$

Thus, equation:

$$dC/dt = K_L a(C_1 - C)/V_L \quad (3)$$

is derived from formulae (1) and (2).

Furthermore, given that $A/V_L$ is represented by a: gas-liquid interface area per unit area, equation:

$$dC/dt = K_L a(C_1 - C) \quad (4)$$

is given.

Since it is difficult to obtain the gas-liquid interface area: a independently in gas-liquid stirring operation, mass transfer volume coefficient for liquid $K_L a$ which is a product of a and mass transfer coefficient for liquid $K_L$ is used as an index to express gas absorbability.

In addition, from the fact that when stirring rate is increased, gas-liquid interface area: a becomes larger, it can generally be said that $K_L a$ becomes larger with stirring rate.

Examples of the organic solvent used in the present reaction include formic acid, acetic acid, methanol, ethanol, N-methylpyrrolidone and the like, and particularly preferred is methanol. These solvents may be used alone, or with a mixture of 2 or more of them. The amount of solvent to be used is 5 to 100 mL, preferably 15 to 25 mL, per 1 g of raw compound.

Examples of the base used in the present reaction include anhydrous sodium acetate, $Et_3N$, pyridine, $NaHCO_3$, $Na_2CO_3$, and the like. In particular, anhydrous sodium acetate and $Et_3N$ are preferred. The amount of base to be used is usually 2 to 3 equivalent moles.

Examples of the catalytic reduction catalyst used in the present reaction include Pd—C, $PtO_2$, Rh—$Al_2O_3$, ($RhCl[P(C_6H_5)_3]_3$) and the like. The amount of catalytic reduction catalyst to be used is 1/10 equivalent mole to 5/1000 equivalent mole, preferably 1/100 equivalent mole to 3/100 equivalent mole relative to 1 mole of raw compound to be used in step (i).

The reaction temperature of the present reaction is usually 10° C. to 100° C., preferably 30° C. to 50° C., and the reaction time is usually 1 to 50 hrs, preferably 2 to 10 hrs.

(E)-2-(1,6,7,8-tetrahydro-2H-indeno[5,4-b]furan-8-ylidene)ethylamine used in the present invention can be used in a form of free compound or a salt thereof. Examples of such salt include a salt with an inorganic acid such as hydrochloric acid, sulfuric acid, and nitric acid, a salt with an organic acid such as formic acid, acetic acid, and trifluoroacetic acid, and the like.

The process for producing (S)-2-(1,6,7,8-tetrahydro-2H-indeno[5,4-b]furan-8-yl)ethylamine or a salt thereof of the present invention is comprised of step (i) for asymmetrically reducing the raw compound: (E)-2-(1,6,7,8-tetrahydro-2H-indeno[5,4-b]furan-8-ylidene)ethylamine or a salt thereof, and step (ii) for converting the side product in the reaction products obtained in step (i) to target compound by catalytic reduction.

The asymmetric reduction in step (i) is carried out by using catalyst, and examples of such catalyst for asymmetric reduction include Ruthenium-optically active phosphine complex (Ru-BINAP), Rhodium-optically active phosphine complex (Rh-BINAP), Iridium-optically active phosphine complex (Ir-BINAP), and the like.

As a Ru-BINAP catalyst, specifically, $Ru_2Cl_4[(R)\text{-BINAP}]_2N(C_2H_5)_3$, {RuCl(Benzene)[(R)-BINAP]}Cl, {RuCl(p-Cymene)[(R)-BINAP]}Cl, {RuBr(p-Cymene)[(R)-BINAP]}Br, {RuI(p-Cymene)[(R)-BINAP]}$I_3$, {RuI(p-Cymene)[(R)-BINAP]}I and the like are exemplified. These catalysts can be prepared according to a known method, for example, methods described in JP-B 07-57758, JP-A 11-140073, etc.

As an asymmetric reduction catalyst, {RuCl(Benzene)[(R)-BINAP]}Cl is preferably used.

When a salt of (E)-2-(1,6,7,8-tetrahydro-2H-indeno[5,4-b]furan-8-ylidene)ethylamine is used as raw compound in the asymmetric reduction reaction of step (i), it is converted to a free compound by alkali treatment, dissolved in organic solvent, and asymmetric reduction catalyst is added to the solution, and then the asymmetric reduction reaction is carried out under pressure and hydrogen atmosphere.

Examples of the organic solvent include aromatic hydrocarbons (e.g., toluene, benzene, etc.), alcohols (e.g., methanol, ethanol, etc.), aliphatic esters (ethyl acetate, n-propyl acetate, n-butyl acetate, etc.), ethers (e.g., isopropyl ether, diethyl ether, tetrahydrofuran (THF), etc.), halogenated hydrocarbons (e.g., dichloromethane, dichloroethane, etc.), amides (e.g., N,N-dimethylformamide, etc.), and the like. These solvents may be used alone, or with a mixture of 2 or more of them, and among them, a mixed solvent of toluene and methanol, a mixed solvent of tetrahydrofuran and methanol, and the like are preferred.

The amount of solvent to be used is 1 to 1000 mL, preferably 2 to 20 mL, per 1 g of raw compound.

The amount to be added of the asymmetric reduction catalyst used in the present reaction is 1/2 equivalent mole to 1/2000 equivalent mole, preferably 1/10 equivalent mole to 1/1000 equivalent mole relative to 1 mole of raw compound, and the hydrogen pressure is 0.5 to 15 MPa, preferably 3 to 11 MPa.

In addition, the reaction temperature is 0 to 150° C., preferably 10 to 80° C., and the reaction time is 0.5 to 200 hrs, preferably 5 to 50 hrs.

The catalytic reduction reaction of the above-mentioned step (ii) is carried out using the reaction solution obtained in step (i). In the reaction solution obtained in step (i), the compound represented by the following formula (III') is included as side product, and in the step (ii), this side product is converted by the catalytic reduction to the target compound, that is, (S)-2-(1,6,7,8-tetrahydro-2H-indeno[5,4-b]furan-8-yl)ethylamine.

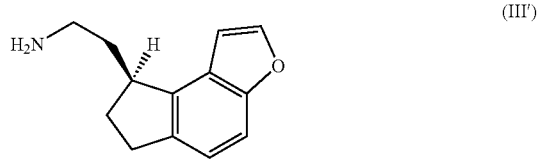

(III')

The reaction of the above-mentioned step (ii) is carried out as follows. That is, to the reaction solution obtained in step (i) is added enough amount of dilute hydrochloric acid to dissolve the reaction product at a temperature below 10° C., and the reaction product is transferred to aqueous layer by stirring or shaking, then the aqueous layer is separated. The obtained aqueous layer is adjusted to pH 3 to 9, preferably 5 to 7, with alkali such as dilute aqueous sodium hydroxide solution, and catalytic reduction catalyst is added thereto to reduce under pressure and hydrogen atmosphere.

Examples of the catalytic reduction catalyst used in the present reaction include Pd—C, PtO$_2$, Rh—Al$_2$O$_3$, (RhCl[P(C$_6$H$_5$)$_3$]$_3$), and the like. The amount of catalytic reduction catalyst to be used is 1/2 equivalent mole to 1/2000 equivalent mole, preferably 1/10 equivalent mole to 1/500 equivalent mole relative to 1 mole of raw compound to be used in step (i), and the hydrogen pressure is 0.5 to 15 MPa, preferably 3 to 11 MPa.

In addition, the reaction temperature is 40° C. to 100° C., preferably 50° C. to 70° C., and the reaction time is 0.5 to 200 hrs, preferably 3 to 20 hrs.

The reaction solution obtained in the catalytic reduction reaction is filtered to remove the catalyst, and treated using a method known per se (e.g., concentration, crystallization, recrystallization, chromatography, etc.) to give (S)-2-(1,6,7,8-tetrahydro-2H-indeno[5,4-b]furan-8-yl)ethylamine.

Furthermore, the resulting (S)-2-(1,6,7,8-tetrahydro-2H-indeno[5,4-b]furan-8-yl)ethylamine can be converted to a desired salt according to a conventional method.

When the reaction and the post-treatment of the above-mentioned step (ii) are carried out without pH control, that is, under a strongly acidic condition below about pH 1, the above-mentioned benzofuran derivative (III') is formed with about 5 to 10% and dihydrobenzofuran dimer (IV') is formed with about 0.2%, which are side products. In contrast, the production amount of these side products can be suppressed to below 0.07%, and to below 0.02%, respectively, by carrying out under the condition of pH 3 to 9, preferably pH 5 to 7 of the present invention.

The process for producing a crystal of (S)—N-[2-(1,6,7,8-tetrahydro-2H-indeno[5,4-b]furan-8-yl)ethyl]propionamide of the present invention will be described below. The process is comprised of step (a) for propionylating the amino group of (S)-2-(1,6,7,8-tetrahydro-2H-indeno[5,4-b]furan-8-yl)ethylamine, and step (b) for crystallizing out of the reaction solution obtained in step (a). Namely, in step (a), the amino group of (S)-2-(1,6,7,8-tetrahydro-2H-indeno[5,4-b]furan-8-yl)ethylamine obtained in the above-mentioned process is reacted with a propionylating agent to propionylate. When the raw material, (S)-2-(1,6,7,8-tetrahydro-2H-indeno[5,4-b]furan-8-yl)ethylamine is used in the form of salt, it is converted to free compound by a conventional method, followed by subjecting to propionylation reaction. Examples of the propionylating agent include propionyl halides such as propionyl chloride and propionyl bromide. The amount of ptopionylating agent to be used is a ratio of 1-2 mol to 1 mol of (S)-2-(1,6,7,8-tetrahydro-2H-indeno[5,4-b]furan-8-yl)ethylamine.

The reaction is carried out in a solvent, and examples of the solvent include ethers such as tetrahydrofuran, diethyl ether, dioxane and 1,2-dimethoxyethane, alcohols such as methanol, ethanol and propanol, hydrocarbons such as benzene, toluene, cyclohexane and hexane, amides such as N,N-dimethylformamide and N,N-dimethylacetamide, halogenated hydrocarbons such as dichloromethane, chloroform, carbon tetrachloride and 1,2-dichloroethane, nitrites such as acetonitrile and propionitrile, sulfoxides such as dimethylsulfoxide, and the like and a mixed solvent thereof, inter alia, tetrahydrofuran is preferred. The reaction time is usually 5 minutes to 48 hrs, preferably 30 minutes to 6 hrs. The reaction temperature is usually −20 to 200° C., preferably −10 to 50° C.

In step (b), crystals of (S)—N-[2-(1,6,7,8-tetrahydro-2H-indeno[5,4-b]furan-8-yl)ethyl]propionamide is crystallized by adding aqueous solvent to the reaction solution obtained in step (a). Examples of the aqueous solvent include city water, pure water, purified water, etc. The amount of aqueous solvent to be added is a ratio by volume of 0.5-5 to the reaction solution obtained in step (a). The crystallization temperature is usually −20 to 60° C., preferably −10 to 40° C.

The crystals of (S)—N-[2-(1,6,7,8-tetrahydro-2H-indeno[5,4-b]furan-8-yl)ethyl]propionamide is obtained with high yield of 97% by collecting the precipitated crystals by filtration. Highly pure crystals of (S)—N-[2-(1,6,7,8-tetrahydro-2H-indeno[5,4-b]furan-8-yl)ethyl]propionamide can be obtained by further recrystallizing the obtained crystals from ethanol-water (1:2).

Although the crystals of (S)—N-[2-(1,6,7,8-tetrahydro-2H-indeno[5,4-b]furan-8-yl)ethyl]propionamide obtained in the process of the present invention may have a possibility of containing the compounds represented by the following formulae (I) to (IV) as impurities (in the present specification, hereinafter, sometimes referred to as compound (I) to (IV), respectively), each content of the compounds (I) to (IV) is 0.15% by weight or less and further total content of the compounds (I) to (IV) is about 0.20% by weight or less.

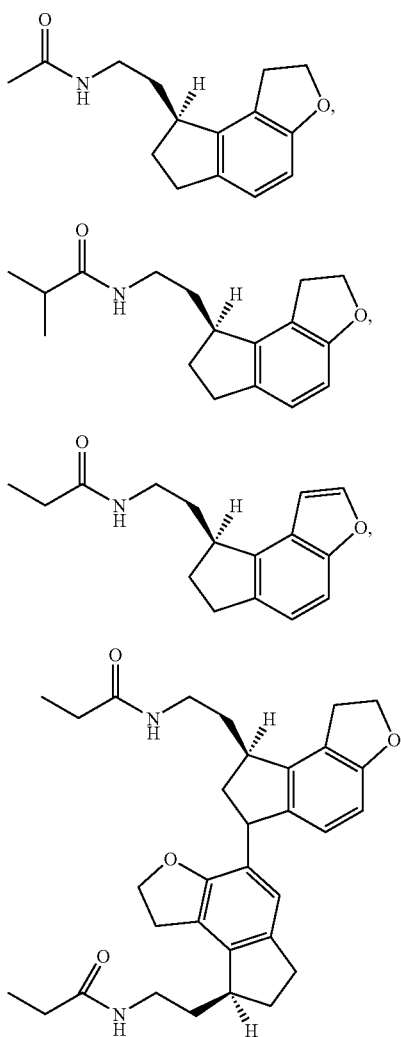

For example, in the crystals of (S)—N-[2-(1,6,7,8-tetrahydro-2H-indeno[5,4-b]furan-8-yl)ethyl]propionamide obtained in the process of the present invention, the contents of compound (III) and (IV) are each below the detection limit of less than 0.02% by weight (HPLC), the content of compound (I) is about 0.1% by weight or less (preferably, 0.03% by weight of 0.03% by weight or less), and the content of compound (II) is about 0.02 to about 0.15% by weight, and further total content of the compounds (I) to (IV) is about 0.20% by weight or less.

or less), and the content of compound (II) is about 0.02 to about 0.15% by weight, and further total content of the compounds (I) to (IV) is about 0.20% by weight or less.

As described above, higher-quality crystals of (S)—N-[2-(1,6,7,8-tetrahydro-2H-indeno[5,4-b]furan-8-yl)]propionamide can be produced by controlling the content of impurities, and as a result, improvement of crystallinity accompanied with improvement of purity, improvement of stability and the like are expected. Furthermore, when (S)—N-[2-(1,6,7,8-tetrahydro-2H-indeno[5,4-b]furan-8-yl)ethyl]propionamide is used as medicine, reduction of impurities has extremely significant meaning from the viewpoint of quality assurance to patients. According to the present invention, such crystals can be produced on a commercial scale. In addition, by using such crystals, the composition of the present invention can be manufactured according to a known method.

(S)—N-[2-(1,6,7,8-tetrahydro-2H-indeno[5,4-b]furan-8-yl)ethyl]propionamide of the present invention has a physiological activity such as affinity for melatonin receptor, in addition, has low toxicity and fewer side effects. Therefore, it can be used for preventing and treating sleep-wakefulness dysrhythmia, jet lag, biorhythm upset due to work in three shifts etc., seasonal melancholia, disease of reproduction and neuroendocrine, senile dementia, Alzheimer's disease, various diseases accompanied with aging (e.g., prevention of aging etc.), cerebral circulation disorder, (cerebral apoplexy etc.), head injury, bone marrow injury, stress, epilepsy, convulsion, anxiety, depression, Parkinson's disease, hypertension, glaucoma, cancer, insomnia, diabetes, cluster headache, and the like, and furthermore, it is also effective for immunomodulation, nootropism, mental stabilization and ovulation adjustment (e.g., contracepyion).

The compounds of the present invention can be used in combination with antidepressant (e.g., imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride, paroxetine hydrochloride, milnacipran hydrochloride, fluoxetine, venlafaxine, Mitrazapine, Sertraline, citalopram, duloxetine, reboxetine, Moclobemide), antianxiety drug (e.g., diazepam, oxazolam, bromazepam, alprazolam, clonazepam, buspirone, tandospirone citrate), mood stabilizer (e.g., lithium, valproic acid, carbamazepine), antidementia drug (e.g., tacrine, donepezil, rivastigmine, galantamine, memantine), antipsychotic drug (e.g., haloperidol, olanzapine, risperidone, quetiapine, ziprasidone, chlorpromazine, sulpiride, Aripiprazole), antiepileptic drug (e.g., phenobarbital, gabapentin, tiagabin, pregabalin), cerebral circulation improving drug, brain metabolic stimulant, and the like.

Examples of administration form include (1) administration of a single preparation obtained by formulating the compound of the present invention and the joint use drug simultaneously, (2) simultaneous administration of two kinds of preparations obtained by formulating the compound of the present invention and the joint use drug separately, via an identical administration route, (3) sequential and intermittent administration of two kinds of preparations obtained by formulating the compound of the present invention and the joint use drug separately, via an identical administration route, (4) simultaneous administration of two kinds of preparations obtained by formulating the compound of the present invention and the joint use drug separately, via different administration routes and (5) sequential and intermittent administration of two kinds of preparations obtained by formulating the compound of the present invention and the joint use drug separately, via different administration routes (e.g. administration in an order of the compound of the present invention→the joint use drug, or administration in a reverse order). A dose of the joint use drug can be selected appropriately based on the clinically used dosage. In addition, a ratio of blending the compound of the present invention and the joint use drug can be appropriately selected depending on an administration subject, an administration route, subject disease, symptom, a combination, and the like. For example, when the administration subject is human, 0.01 to 100 parts by weight of the joint use drug can be used relative to 1 part by weight of the compound of the present invention.

(S)—N-[2-(1,6,7,8-tetrahydro-2H-indeno[5,4-b]furan-8-yl)ethyl]propionamide of the present invention can be used as a pharmaceutical raw material with grinding by Jet mil etc., and a content uniformity in preparation and the like can be assured by adjusting the particle size (median size) to about 1 to 10 μm.

The particle size can be measured as follows by using commercially available measuring apparatus.

A 100 mL Erlenmeyer flask equipped with stopper is charged with 0.05 g of sample, and 50 mL of dispersion medium is added thereto. The mixture is irradiated with ultrasonic wave for about 5 minutes with shaking and mixing to give a suspension. To 40 mL of dispersion medium is added about 100 μL of this suspension, and a test is carried out under the following condition.

[Dispersion Medium]

0.1% sodium lauryl sulfate solution saturated with (S)—N-[2-(1,6,7,8-tetrahydro-2H-indeno[5,4-b]furan-8-yl)ethyl]propionamide

[Apparatus]

HELOS system KF (Sympatec GmbH)

HELOS sensor CUVETTE dispersion unit (wet disperser)

HELOS standard software: WINDOX 3.2 (for Windows) or equivalent

[Condition for Measurement]

Focal length: 100 mm

Stirring speed: 50%

Sampling time: 1 second

Measurement time: 10 seconds

The compound of the present invention can be safely administered orally or parenterally (e.g. local, rectal, intravenous administration etc.) as it is or by formulating into pharmaceutical preparations such as tables (including sugar-coated tablets, film coating tablets), powders, granules, capsules, solutions, emulsions, suspensions, injectables, suppositories, sustained-release agents and adhesive preparations by mixing with a pharmacologically acceptable carrier according to a conventional method (e.g., method described in Japanese Pharmacopoeia, etc.). A content of the compound in the pharmaceutical composition is usually about 0.01 to 100% by weight based on the whole composition.

The present invention will be further explained in detail by way of the following Reference Examples and Examples, but the present invention is not limited to these Examples. In addition, each abbreviation in the Reference Examples and Examples has the following meanings.

DBF: 2,3-dihydrobenzofuran

FBA: 2,3-dihydrobenzofuran-5-carbaldehyde

PPN: ethyl (E)-3-(2,3-dihydrobenzofuran-5-yl)propenoate

PPE: ethyl 3-(2,3-dihydrobenzofuran-5-yl)propionate

DBA: 3-(6,7-dibromo-2,3-dihydrobenzofuran-5-yl)propionic acid

BIF: 4,5-dibromo-1,2,6,7-tetrahydro-8H-indeno[5,4-b]furan-87-one

THI: 1,2,6,7-tetrahydro-8H-indeno[5,4-b]furan-8-one

ICN: (E)-(1,6,7,8-tetrahydro-2H-indeno[5,4-b]furan-8-ylidene)acetonitrile

EAI.HCl: (E)-2-(1,6,7,8-tetrahydro-2H-indeno[5,4-b]furan-8-ylidene)ethylamine hydrochloride (S)-AMI.HCl: (S)-2-(1,6,7,8-tetrahydro-2H-indeno[5,4-b]furan-8-yl)ethylamine hydrochloride

REFERENCE EXAMPLE 1

2,3-Dihydrobenzofuran-5-carbaldehyde

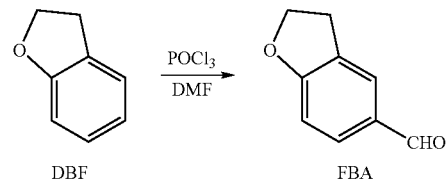

2,3-Dihydrobenzofuran (100 g, 832 mmol) and N,N-dimethylformamide (134 g, 1830 mmol) were mixed and heated, and phosphorus oxychloride (255 g, 1643 mmol) were added thereto at an inner temperature of 70 to 80° C. over 2 hrs. The reaction mixture was heated at an inner temperature of 80 to 90° C. and stirred for 7.5 hrs. Then, the resulting mixture was added dropwise to water (1000 g) under cooling, and stirred at room temperature for 5 hrs. The resulting mixture was extracted with toluene, and the extract was washed sequentially with water, saturated sodium bicarbonate aqueous solution and water, and the organic layer was concentrated under vacuum to give a toluene solution of the title compound (amount 340 g, apparent yield 100%).

REFERENCE EXAMPLE 2

Ethyl (E)-3-(2,3-dihydrobenzofuran-5-yl)propenoate

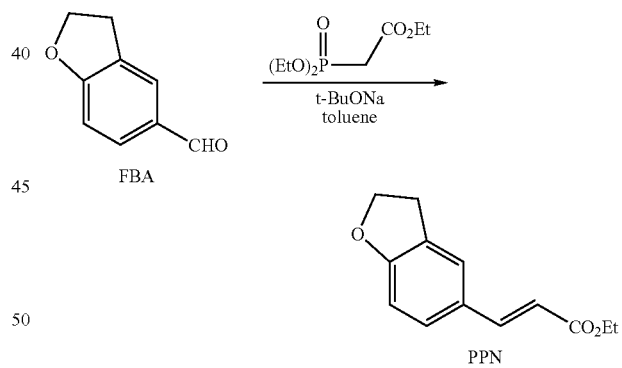

To the solution (340 g) of 2,3-Dihydrobenzofuran-5-carbaldehyde (832 mmol) in toluene obtained in the above step was added dropwise triethyl phosphonoacetate (205 g, 916 mmol) under cooling. Then, a suspension of sodium t-butylate (88.0 g, 1187 mmol) in toluene (530 g) was added dropwise, and stirred for 1 hr, and further acetic acid (20 g) and water (500 g) were added dropwise thereto. The reaction mixture was warmed to room temperature, and separated the layers. The organic layer was washed sequentially with saturated sodium bicarbonate aqueous solution and water, and the organic layer was concentrated to below 300 mL under vacuum. Then to the residue was added methanol (396 g) to heat and dissolve. To the solution was added dropwise water (500 g) at room temperature, and stirred to deposit crystals, which was collected by filtration and dried under reduced pressure to give title compound (amount 161 g, yield 88.1%).

REFERENCE EXAMPLE 3

Ethyl 3-(2,3-dihydrobenzofuran-5-yl)propionate

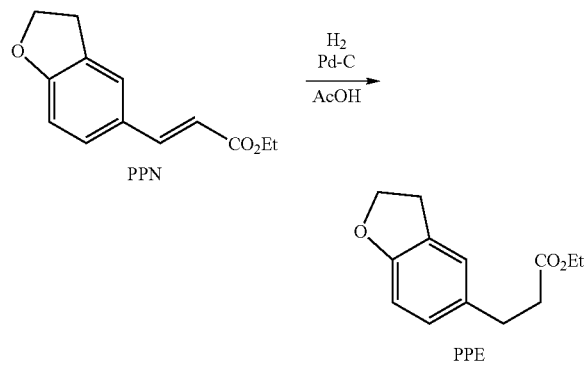

Ethyl (E)-3-(2,3-dihydrobenzofuran-5-yl)propenoate (50.0 g, 227 mmol) was dissolved in acetic acid (312 g), and the reaction system was replaced with nitrogen. Then, 5% Pd/C (4.96 g, as dry weight) was added to the solution and pressurized with hydrogen to 196 to 294 kPa. The mixture was reacted at 50° C. for 1 hr under a pressure of 196 to 294 kPa. The catalyst was filtered, and washed with acetic acid (208 g) to give a solution of the title compound in acetic acid (amount 569 g, apparent yield 100%).

REFERENCE EXAMPLE 4

3-(6,7-Dibromo-2,3-dihydrobenzofuran-5-yl)propionic acid

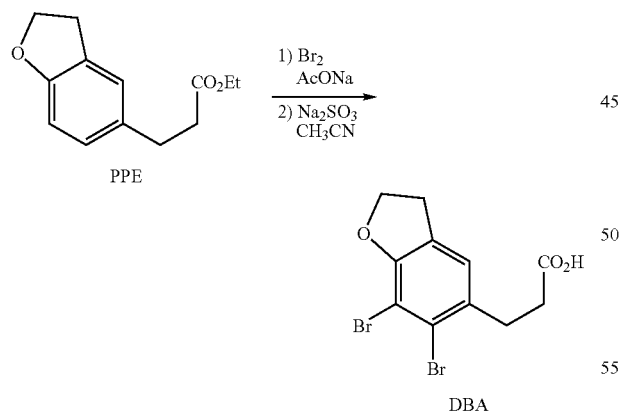

To the solution of PPE in acetic acid (569 g, 227 mmol) obtained in the above step was added anhydrous sodium acetate (18.6 g), and bromine (222 g) was added dropwise thereto under stirring and cooling over 2 hrs. After reacting for 4 hrs at room temperature, the reaction mixture was added dropwise to a cooled 15% aqueous solution of sodium sulfite (670 mL), and stirred for 30 minutes. To the reaction solution was added acetonitrile (118 g), and reacted for 2 hrs with heating under reflux, then cooled gradually and stirred for 1 hr to crystallize. The crystals were collected by filtration, washed with water, and dried under vacuum to give title compound (amount 63.3 g, yield 73.2%).

REFERENCE EXAMPLE 5

4,5-Dibromo-1,2,6,7-tetrahydro-8H-indeno[5,4-b]furan-8-one

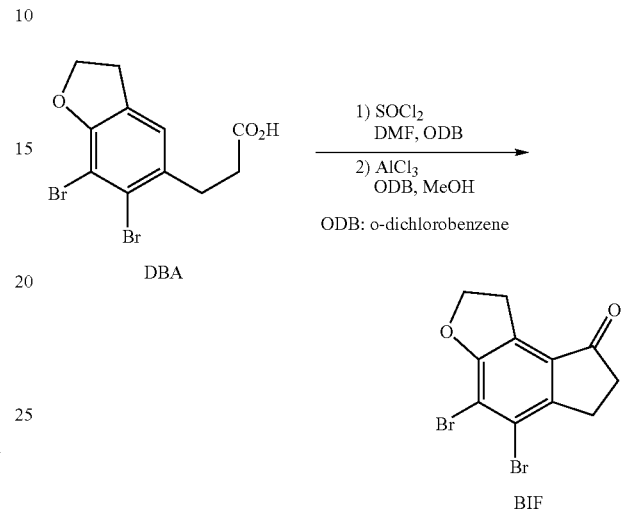

3-(6,7-Dibromo-2,3-dihydrobenzofuran-5-yl)propionic acid (40.0 g, 114 mmol), o-dichlorobenzene (182 g) and N,N-dimethylformamide (0.1 g) were mixed, and thionyl chloride (17.7 g, 149 mmol) was added dropwise thereto at inner temperature of 42° C., followed by stirring for 30 to 40 minutes to give a solution of acid chloride. Then, to the solution was added anhydrous aluminium chloride (17.5 g, 132 mmol) in several portions under ice-cooling, and stirred for 30 minutes. Methanol (475 g) was prepared separately, and the reaction solution was added dropwise to the methanol to crystallize. To the crystallization solution was added dropwise water (76 g) under cooling, and stirred for 30 minutes. The crystals were collected by filtration, and the wet crystals were washed sequentially with methanol, water, saturated aqueous solution of sodium bicarbonate, water, and methanol, followed by drying under vacuum to give 31.6 g of title compound (yield 92.2%).

EXAMPLE 1

1,2,6,7-Tetrahydro-8H-indeno[5,4-b]furan-8-one

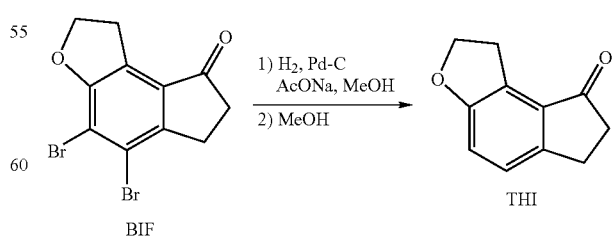

(1) 4,5-Dibromo-1,2,6,7-tetrahydro-8H-indeno[5,4-b]furan-8-one (280 kg, 843 mol), anhydrous sodium acetate (173 kg, 2109 mol), methanol (6384 L) were mixed, and the reaction system was replaced with nitrogen. Then, to the reaction mixture was added 10% Pd/C (30.8 kg, as dry weight), and pressurized with hydrogen to 0.29 to 0.49 MPa, and catalytically reduced at about 40° C. for 8 hrs with stirring at such a stirring rate that the gas-liquid overall mass transfer coefficient $K_L a$ (1/hr) is about 15. The catalyst was filtered, and the filtrate was concentrated under reduced pressure, and further water was added to the residue, followed by concentrating under reduced pressure to substitute the solvent, cooling and stirring for 1 hr to mature. The crystallization solution was filtered to give wet crystals of title compound (amount 127 kg as dry weight, yield 86.6%). The content of dimer in the wet crystals was less than 0.1% by weight.

(2) Purification Step

Wet crystals (127 kg as dry weight), activated charcoal (6 kg, Shirasagi A: trade name) and methanol (1723 L) were mixed, and stirred for 1 hr under reflux, and filtered. The filtrate and washings were concentrated under reduced pressure, then, the residue was refluxed for 1 hr and cooled. Water (306 L) was added thereto under cooling, matured for 1 hr, and the precipitate was collected by filtration, followed by drying under reduced pressure to give title compound (amount 117 kg, yield 92.1%).

(3) Gas-Liquid Overall Mass Transfer Coefficient

Here, the gas-liquid overall mass transfer coefficient was determined by $Na_2SO_3$ method.

1) $Na_2SO_3$ method (sodium sulfite method)

(a) Principle

Sodium sulfite ($Na_2SO_3$), in an aqueous solution thereof, converts to sodium sulfate ($Na_2SO_4$) by reacting with oxygen which was incorporated from air. The reaction rate is sufficiently fast compared to absorption rate of oxygen (oxygen absorption is rate-determining step). Therefore, oxygen absorption rate ($N_A$) can be obtained by measuring the concentration change of sodium sulfite.

Now, the gas-liquid overall mass transfer volume coefficient $K_L a$ is defined by the following equation.

$$N_A = K_L a (C^* - C)$$

Since actually in this measurement system, concentration of dissolved oxygen in the aqueous solution of sodium sulfite can be deemed as 0, the following equation is given.

$$K_L a = N_A / C^*$$

On the other hand, solubility of oxygen in aqueous solution can be expressed by the following, using Henry's law.

$$C^* = p/H$$

From these, $K_L a$ can be calculated.

In addition, symbols in the above equation have the following meanings.

$K_L a$: gas-liquid overall mass transfer volume coefficient [1/Hr]
$N_A$: oxygen absorption rate [mol/L·Hr]
C: oxygen concentration in liquid [mol/L]
$C^*$: solubility of oxygen in saturation [mol/L]
p: partial pressure of oxygen in gas phase [Pa]
H: Henry constant [Pa·L/Hr]

(b) Measurement Method (i) Pure water (475 ml, same liquid volume as feed scale of BIF 23.34 g) is charged into 1 L autoclave (Glass Reactor, TEM-V-1000 type).
(ii) $Na_2SO_3$ (9.5 g) is added thereto, and mixed for about 2 minutes to dissolve.
(iii) A prepared 0.1 mol/L $CuSO_4$ solution (4.75 ml) is added to the aqueous solution of $Na_2SO_3$ ($CuSO_4$ concentration after the addition=$1 \times 10^{-3}$ M), and the reaction solution is stirred slowly for 1 minute (reaction initiation).
(iv) Immediately, 10 ml of the dissolution solution is precisely sampled, and titrated according to the procedure of the following (c). (titration volume=$T_1$ [ml])
(v) The reaction solution is stirred with a given rotation rate for a given time $\Delta\theta$ (=1.0 [Hr]). At this time, a certain amount of air is streamed into the upper of the vessel to prevent decrease in partial pressure of oxygen in gas phase in autoclave (about 200 ml/L).
(vi) 10 ml is precisely sampled from the solution of (v), and titrated according to the procedure of the following (c). (titration volume=$T_2$ [ml])
(vii) From the result of titration, oxygen absorption rate $N_A$ is calculated according to the following equation. Here, F represents a factor of N/10 iodine solution reagent.

$$N_A = \frac{0.1 \times F}{4 \times 10 \times \Delta\theta}(T_1 - T_2)$$

(c) Titration method (method for titration of sodium sulfite)*[1]

*[1]: Titration principle is based on that after oxidizing sulfite radical existing in the sample solution with iodine, the remaining iodine is titrated with sodium thiosulfate, and each step can be represented by the following reaction formula.

oxidation of sulfite radical: $Na_2SO_3 + I_2 + H_2O \rightarrow 2NaI + H_2SO_4$ titration of iodine: $I_2 + 2Na_2S_2O_3 \rightarrow 2NaI + Na_2S_4O_6$ (i) A 200 ml Erlenmeyer flask containing pure water (100 m), acetic acid-sodium acetate buffer*[2] (10 ml), and N/10 iodine solution reagent (40 ml) is prepared beforehand.
*[2]: 75 g of sodium acetate ($CH_3COONa \cdot 3H_2O$) is dissolved in 500 ml of aqueous acetic acid ($CH_3COOH:H_2O=1:2$).
(ii) Sample solution (10 ml) is added thereto gently.
(iii) After about 5 minutes, the sample solution is titrated with N/10 sodium thiosulfate solution using a starch solution*[3] (0.5-1 ml) as an indicator.
*[3]: 1.0 g of starch is scrubbed and mixed with 10 ml of water, and the resulting mixture is fed into 200 ml of hot water. After boiling until this turns into semi-transparent, it is left to cool.

REFERENCE EXAMPLE 6

(E)-(1,6,7,8-Tetrahydro-2H-indeno[5,4-b]furan-8-ylidene)acetonitrile

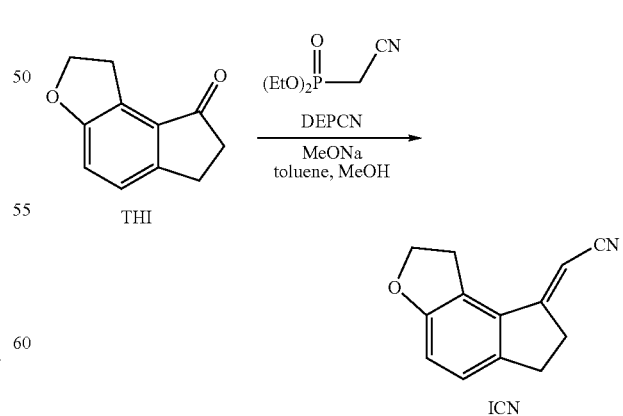

To a solution of toluene (184 g), 1,2,6,7-tetrahydro-8H-indeno[5,4-b]furan-8-one (8.5 g, 48.9 mmol) and diethyl cyanomethylphosphonate (10.4 g, 58.7 mmol) was added dropwise 28% sodium methoxide solution in methanol (11.3 g) over 1 hr under ice-cooling, and reacted for 4 hrs. To the reaction solution was added dropwise water (85 μg), and warmed, then the layers were separated. The organic layer was washed with water, and filtered to remove dusts under pressurization. The organic layer was concentrated under reduced pressure, and to the residue was added methanol and concentrated under reduced pressure to substitute the solvent. After stirring for 1 hr under heating with reflux, the solution was cooled and matured for 1 hr. The crystallization solution was filtered, and the crystals were dried under reduced pressure to give title compound (amount 8.1 g, yield 84.4%).

REFERENCE EXAMPLE 7

(E)-2-(1,6,7,8-Tetrahydro-2H-indeno[5,4-b]furan-8-ylidene)ethylamine hydrochloride

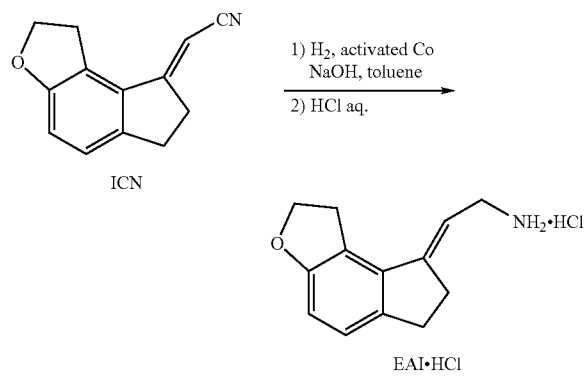

To a mixed suspension of (E)-(1,6,7,8-tetrahydro-2H-indeno[5,4-b]furan-8-ylidene)acetonitrile (10.0 g, 50.7 mmol) in toluene (37.5 mL) and methanol (12.5 mL) were added activated cobalt (7.22 g) and 14.4% aqueous solution of potassium hydroxide (1.4 g), and stirred for 6.5 hrs at 34 to 50° C. under hydrogen atmosphere (0.2 MPa). The reaction solution was filtered, and to the filtrate were added toluene (170 mL) and methanol (35 mL) to separate the layers. 0.5N Hydrochloric acid (101 mL) was added to the organic layer, and stirred for 30 minutes at 25 to 30° C. Then, the layers were separated, and active charcoal (1 g) was added to the aqueous layer, followed by stirring. The active charcoal was removed, by filtration to give an aqueous solution of title compound (246 g, Net 12.0 g, yield 99.6%).

EXAMPLE 2

(S)-2-(1,6,7,8-Tetrahydro-2H-indeno[5,4-b]furan-8-yl)ethylamine hydrochloride

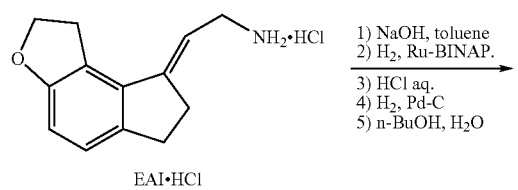

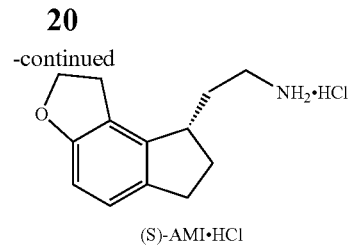

To an aqueous solution of (E)-2-(1,6,7,8-tetrahydro-2H-indeno[5,4-b]furan-8-ylidene)ethylamine hydrochloride (1979 kg, Net 122 kg, 513 mol) were added toluene (532 L) and 5% aqueous solution of sodium hydroxide (456 L), and stirred. The layers were separated, and to the organic layer were added methanol (155 kg) and [RuCl(benzene)(R)-BINAP]Cl (894 g) under nitrogen atmosphere, followed by stirring at 80° C. for 15 hrs under hydrogen atmosphere (4.9 MPa). The reaction solution was cooled, and water (330 L) and concentrated hydrochloric acid (52.3 kg) were added at below 30° C., followed by stirring for 30 minutes, then the layers were separated. The aqueous layer was washed with toluene (195 L), and pH was adjusted to about 6.0 by adding 5% aqueous solution of NaOH to the aqueous layer. (containing 5.0% of compound III'). 5% Pd—C (50% wet, 9.7 kg) was added thereto, and stirred at 60° C. for 6 hrs under hydrogen atmosphere (4.9 MPa). The reaction mixture was filtered, and the filtrate was adjusted to around pH 6.0 with 5% aqueous solution of NaOH or dilute hydrochloric acid, followed by concentration under reduced pressure. The residue was recrystallized from mixed solution of n-butanol and water to give title compound (88.6 kg, yield 73.0%, compound (III') is not detected, compound (IV') is not detected).

In addition, the content of compound (III') and compound (IV') (dimer) in the obtained crystals of the title compound was determined by HPLC under the following condition.

detector: ultraviolet absorptiometer (wavelength for measurement: 220 nm)
column: Develosil UG-3, 4.6 mmi.d.×75 mm
column temperature: given temperature around 25° C.
mobile phase: mixed solution of 0.1 mol/L potassium dihydrogenphosphate (pH 3.0)/methanol (75:25)

EXAMPLE 3

(i) (S)—N-[2-(1,6,7,8-Tetrahydro-2H-indeno[5,4-b]furan-8-yl)ethyl]propionamide

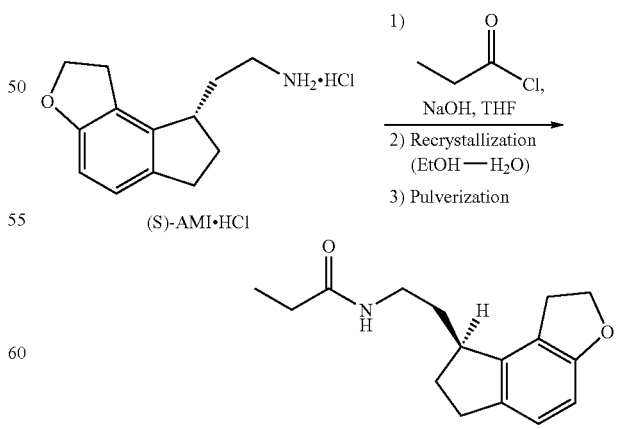

To a mixed solution of (S)-2-(1,6,7,8-tetrahydro-2H-indeno[5,4-b]furan-8-yl)ethylamine hydrochloride (74 kg, 309 mol) in tetrahydrofuran (185 L) and city water (259 L) were added 30% aqueous solution of sodium hydroxide (70 L) and propionyl chloride (32.8 kg), and stirred at room temperature for 1 hr. To the reaction solution was added city water (592 L), and cooled. The precipitated crystals were collected by filtration, and dried under reduced pressure to give title compound (78.0 kg, yield 97.4%).

(ii) Purification Step

The crystals (77.3 kg, 298 mol) obtained in (i) were dissolved in mixed solution (178 kg) of ethanol and purified water (10:1), and active charcoal (0.78 kg) was added thereto, then stirred for 10 minutes, followed by filtration (washed with mixed solution (74 kg) of ethanol and purified water (10:1)). To the filtrate was added water (588 L) under warming, cooled, and the precipitated crystals were collected by filtration, which were dried under reduced pressure. The resulting crystals were pulverized with jet mil to give title compound (74.0 kg, yield 95.7%, compound (I) 0.02%, compound (II) 0.06%, compound (III) and (IV) less than 0.02%, total analogous material 0.08%).

(iii) Analysis Condition

The content of compound (I) to (IV) in the crystals of the title compound obtained in (ii) was determined by HPLC under the following condition.

detector: ultraviolet absorptiometer (wavelength for measurement: 288 nm)

column: YMC-Pack ODS-AM AM-302.5 um, 4.6 mm i.d.× 150 mm (manufactured by YMC)

column temperature: given temperature around 25° C.

mobile phase: A; mixed solution of 0.01 mol/L phosphate buffer (pH 7.0)/acetonitrile (4:1)
B; mixed solution of 0.01 mol/L phosphate buffer (pH 7.0)/acetonitrile (3:7)

Gradient Condition

| time (min.) | mobile phase A | mobile phase B |
|---|---|---|
| 0 | 90% | 10% |
| 60 | 40% | 60% |
| 70 | 40% | 60% |
| 70.1 | 90% | 10% |
| 85 | 90% | 10% |

Resulting HPLC chart was shown in FIG. 1. As obvious from FIG. 1, compound (I) and (II) were detected at each side of main peak of (S)—N-[2-(1,6,7,8-tetrahydro-2H-indeno[5,4-b]furan-8-yl)ethyl]propionamide, however, compound (III) and (IV) were each below the detection limit of less than 0.02%.

INDUSTRIAL APPLICABILITY

According to the process of the present invention, by controlling the pH of reaction solution in catalytic reduction step and post-treatment solution thereof, highly pure optically active amine derivatives which are useful as medicine can be produced with high yield, and high-quality pharmaceutical raw materials can be provided industrially.

The invention claimed is:

1. A process for producing (S)-2-(1,6,7,8-tetrahydro-2H-indeno[5,4-b]furan-8-yl)ethylamine or a salt thereof, which comprises step (i): a step for asymmetrically reducing (E)-2-(1,6,7,8-tetrahydro-2H-indeno[5,4-b]furan-8-ylidene)ethylamine or a salt thereof with a catalyst, and step (ii): a step for catalytically reducing the reaction product obtained in step (i) at a reaction temperature of 40° C. to 100° C. and pH 3 to 9 with a catalyst.

2. The process according to claim 1, wherein the reaction temperature in step (ii) is 50° C. to 70° C.

3. The process according to claim 1, wherein the pH in step (ii) is 5 to 7.

4. The process according to claim 1, wherein the catalyst in step (i) is Ru-BINAP catalyst.

5. The process according to claim 1, wherein the catalyst in step (ii) is Pd—C catalyst.

* * * * *